(12) United States Patent
Verink

(10) Patent No.: US 6,929,745 B2
(45) Date of Patent: Aug. 16, 2005

(54) APPARATUS FOR THREE-PHASE SEPARATION DURING TREATMENT OF WASTEWATER AND SLUDGE

(76) Inventor: Johan Verink, Kaulbachstrasse 26, Hannover (DE), 30625

( * ) Notice: Subject to any disclaimer, the term of this patent is extended or adjusted under 35 U.S.C. 154(b) by 72 days.

(21) Appl. No.: 10/331,169

(22) Filed: Dec. 30, 2002

(65) Prior Publication Data

US 2003/0150786 A1 Aug. 14, 2003

Related U.S. Application Data

(63) Continuation of application No. PCT/DE01/02298, filed on Jun. 26, 2001.

(30) Foreign Application Priority Data

Jun. 30, 2000 (DE) ......................... 100 31 093

(51) Int. Cl.$^7$ ................................. C02F 3/00
(52) U.S. Cl. ....................... 210/603; 210/608; 210/188; 95/241; 95/254; 95/262; 96/155
(58) Field of Search ................................ 210/603, 608, 210/188; 95/241, 254, 262; 96/155, 220

(56) References Cited

U.S. PATENT DOCUMENTS 5,500,118 A * 3/1996 Coenen et al. .............. 210/603

FOREIGN PATENT DOCUMENTS

| CH | 648594 | 3/1985 | |
|----|--------|--------|---|
| DE | 3904326 | 8/1990 | |
| DE | 4212015 | 10/1992 | |
| DE | 4320096 | 12/1994 | |
| EP | 0096825 | 12/1983 | |
| EP | 300348 A2 * | 1/1989 | .............. 210/532.1 |
| EP | 0808805 | 11/1997 | |

* cited by examiner

Primary Examiner—Robert A. Hopkins
(74) Attorney, Agent, or Firm—Crowell & Moring LLP

(57) ABSTRACT

An apparatus for carrying out a three-phase separation during treatment of wastewater and sludge, which includes a gas collector (1) which traps gases that rise in the settling basin during the treatment process. The gas collector has an inclined outer surface (2, 3) which ensures that sewage sludge can slide down unhindered. The angle of inclination (α) can be adjusted in order to adapt the apparatus to different sewage sludges. The gas collector has a flexible tube (4) which is guided around a plurality of reversing or bending surfaces (5, 6, 7, 8) so that sections (10, 11) of the tube form the inclined outer surfaces (2, 3). Another section (15) of the tube defines the interior volume (V) of the gas collector. The resulting gas collector is simple to produce and effectively prevents the separation apparatus from becoming clogged by particles of sewage sludge adhering to the outer surfaces of the gas collector.

17 Claims, 3 Drawing Sheets

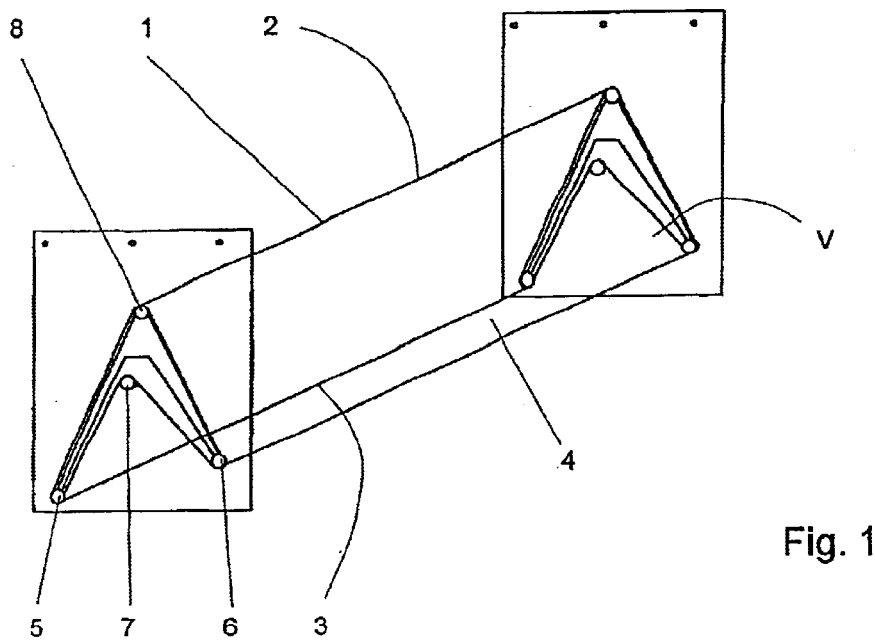
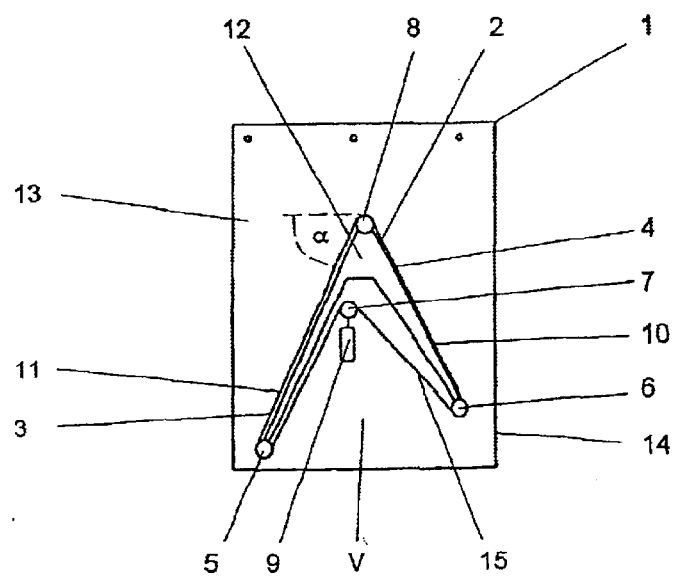

APPARATUS FOR THREE-PHASE SEPARATION DURING TREATMENT OF WASTEWATER AND SLUDGE

CROSS REFERENCE TO RELATED APPLICATION

This application is a continuation of international patent application No. PCT/DE01/02298, filed Jun. 26, 2001, designating the United States of America, and published in Germany as WO 02/02467, the entire disclosure of which is incorporated herein by reference. Priority is claimed based on Federal Republic of Germany patent application no. DE 100 31 093.1, filed Jun. 30, 2000.

BACKGROUND OF THE INVENTION

The present invention relates to an apparatus for three-phase (i.e., solid/liquid/gas) separation during treatment of wastewater and sludge, having a gas collector, positioned in a settling basin, for capturing the gas arising during the conversion process in the apparatus for three-phase separation or gas introduced therein, the gas collector having an outer surface which allows sewage sludge to slide off and which is slanted in relation to the horizontal.

Such an apparatus for three-phase separation is used for the purpose of capturing, in the gas collector, the fermentation gases arising during the aerobic or anaerobic conversion process or the gases supplied during aerobic treatment. These gases are then available, in the first case cited, as an energy source for a further use, to operate the apparatus or even for other purposes, or, in the second case cited, for odor removal, for example.

For this purpose, it is known to construct the gas collector with an angular form in such a way that it has two legs which form the slanted outer surface and simultaneously enclose a volume, into which the gas may flow unhindered from underneath. The sewage sludge introduced from above slides essentially unhindered off of the slanted outer surface of the gas collector and settles on the bottom of the basin. The usable gas arising during the subsequent conversion process rises upward and reaches the gas collector. Adjacent gas collectors advantageously have a slight overlap in this case, through which a loss of gas, which could otherwise rise upward unhindered through the intervening space to the water surface, is prevented. In this case, the downwardly moving sewage sludge may possibly slide from one outer surface onto the outer surface of an adjacent gas collector, the distance between adjacent gas collectors being dimensioned in such a way that blockage of the intermediate space is prevented. Multiple gas collectors may be positioned next to one another and in multiple planes above one another, in order to thus increase the capacity of the apparatus for three-phase separation. It has been found to be good practice to provide an angle of inclination relative to horizontal of between 50° and 70°, as a result of which both reliable sliding off of the introduced sewage sludge and also large-area, and therefore unproblematic, capture of the rising gas may be achieved simultaneously.

The gas collector is typically assembled on site from prefabricated components or from concrete or plastic, so that it is possible to achieve any desired expansion in size in one plane and/or in further planes on top of one another.

It has been found to be disadvantageous during operation of such three-phase separation apparatus that the consistency of the sewage sludge to be treated often varies greatly. As a result, the sewage sludge may adhere or build up on the outer surface of the gas collector. In order to counteract this, it is necessary to previously investigate and possibly pre-treat the sewage sludge, which results in undesirably high treatment costs. If blockage of the intermediate spaces nonetheless occurs, then a costly manual cleaning is necessary.

SUMMARY OF THE INVENTION

It is an object of the present invention to provide an improved gas collector for apparatus for three-phase separation in the treatment of wastewater and sludge.

Another object of the invention is to provide a gas collector for apparatus for three-phase separation which avoids in a simple way adherence of sludge solids to the outer surface of the gas collector and possible blockage of the intermediate spaces.

A further object is to provide an apparatus for three-phase separation which renders it unnecessary to preliminarily analyze or pre-treat sludge introduced into it.

These and other objects are achieved in accordance with the present invention by providing an apparatus for three-phase separation during treatment of wastewater and sludge comprising a gas collector disposed in a settling basin for capturing gas which arises during the treatment or is introduced therein, said gas collector having an outer surface which is inclined relative to horizontal and allows the sewage sludge to slide off, in which the outer surface has an angle of inclination which may be adjusted to adapt the apparatus to treatment of different sewage sludges.

Further advantageous embodiments and refinements of the invention are described hereinafter.

Thus, according to the present invention, an apparatus for three-phase separation is provided in which the outer surface has an angle of inclination which may be adjusted to adapt the apparatus to different sewage sludges. It thus becomes possible to achieve rapid adjustment to different sewage sludges in a simple way. The undesired adherence of the sewage sludge to the gas collectors and the accumulation and/or clogging, in some circumstances, in the intermediate spaces between adjacent gas collectors is thereby reliably prevented. For this purpose, the outer surface is movably arranged through a movable mount or joint. With such an apparatus it is possible, for example, to dislodge already adhering sewage sludge by temporarily setting a large angle of inclination. Therefore, deposits of sludge may be minimized or readily removed. The angle of inclination may be adjusted either manually or using a drive motor, e.g., an electric motor. Consequently, it is not necessary to determine in advance the characteristic properties of the sewage sludge or to pre-treat the sludge, with the result that the expense of successful treatment of the wastewater may be reduced.

A particularly advantageous embodiment of the present invention is also provided if the gas collector has two outer surfaces, slanted toward one another, whose angles of inclination may be set independently from one another. In this way, the apparatus may be adjusted without difficulty to accommodate the varying properties of different sewage sludges, as well as varying spatial distributions of the sewage sludge in the settling basin, which sometimes also requires a different angle of inclination in some sections of the apparatus.

Another particularly advantageous refinement of the present invention is also achieved in that the angle of inclination of the outer surface which is set, also determines the respective volume of the gas collector available to receive the gas that arises. In this way, a change of the angle of inclination of the outer surface simultaneously also leads to a changed capacity of the gas collector, so that simple adjustment is simultaneously achieved. In this case, a greater angle of inclination leads directly to a greater gas volume, which may therefore be captured without a problem. The respective angles of inclination of a gas collector provided with two outer surfaces slanted toward one another may be adjusted either corresponding to one another or independently from one another.

A refinement of the present invention in which the angles of inclination of a plurality of adjacent gas collectors are adjustable by a shared drive is also particularly advantageous. In this way, simple movement of the outer surface is achieved by a uniform adjustment of the neighboring gas collectors. Mutual interference of neighboring gas collectors by differing angles of inclination and resultant non-uniform settling is therefore precluded. The outer surfaces of the different gas collectors may also be de-coupled so as to be movable independently or differently from one another, e.g., for repair purposes.

The undesired adhesion of sludge is particularly effectively avoided if the angle of inclination is continuously changeable by a drive. In addition, already adhering sludge may be removed without difficulty through continuous movement, which may be produced, for example, using a cam drive.

Another advantageous embodiment of the present invention is also provided if the outer surface comprises a flexible section. In this way, simple adjustment of the angle of inclination may be achieved through elastic deformation of the outer surface. Furthermore, it is thus possible, through deformation which changes in rapid sequence, to detach particles of sewage sludge which may have adhered to the outer surface and remove already adhering material. In this case, for example, curvatures which improve the sliding off of the sewage sludge may also be established, for example.

For this purpose, it is also particularly advantageous if the outer surface comprises a gas-tight sheet material or a fabric. In this way, any desired deformation of the outer surface may be achieved, which may be adjusted as a function of the significant parameters of the sewage sludge. The gas-tight sheet material and/or gas-tight fabric may be mounted under tension for this purpose on a suitable support, or even initially hang free and only receive its predetermined shape when wastewater and sludge are introduced into the apparatus.

Another advantageous embodiment of the present invention is provided if the gas collector has a tensioning device for the outer surface. In this way, a tension of the outer surface may be established, which is adapted to the character of the sewage sludge to be introduced into the apparatus, by means of which the desired form is imparted to the separator and the surface character of the outer surface is determined. The stretching of the outer surface which may also be achieved in this way, thereby effectively prevents possible adhesion of the sewage sludge.

It is also particularly advantageous if the tensioning device comprises a spring element. By suitable positioning of the spring element, a constant tension on the outer surface can be established, which can be influenced in such a way by sewage sludge which may adhere thereto that the tension changes and the sewage sludge is dislodged. For this purpose, the spring element may be constructed, for example, as a tension spring and engage a free end of the outer surface. Or it also may be configured as a compression spring which presses against a rear area of the outer surface in order to transmit the necessary tension to the outer surface.

The tension may also be set particularly easily if the tensioning device comprises buoyant float member. Buoyant lifting forces arising in the settling basin are thereby used in order to apply the necessary tension to the outer surface. In this way, particularly simple positioning of the gas collector may be achieved through equalization of the lift, which is adjustable for this purpose, and the downward gravitational forces caused by its own weight.

It is thereby especially advantageous if the float is made of bamboo. Through its enclosed air chambers, this material allows simple adjustment of the desired buoyant lifting forces, whereby some or all of the air chambers may be broken open to reduce the lift. Furthermore, the intermediate walls of the air chambers may be removed and a simple conduit may thus be provided. Furthermore, bamboo is available in nearly unlimited quantities precisely in those countries important for economic development.

A particularly advantageous variant of the present invention is also achieved if the gas collector has a movable surface, supported on a plurality of reversing or bending surfaces, having a first section forming the outer surface and a second, set back section to receive the arising gas. In this way, the component is simultaneously used in a simple way on the outside as an outer surface and on the inside as a container. The production cost is thus reduced to a few components, which may be assembled without difficulty from molded parts.

For this purpose, it is also particularly advantageous if the flexible surface comprises a tube or hose. Such a hose may be formed without difficulty into the desired inclined outer surface by individual reversing or bending surfaces positioned in the inside of the hose, and the volume intended for capturing the gas can be formed by a further reversing or bending surface that presses against the hose from outside. An edge configuration which is unfavorable for durability is thereby avoided, in that only a simple reversing or bending surface is necessary. At the same time sewage sludge which contact the upper surfaces is spatially separated from the captured gas by an insulating intermediate space, which lies adjacent different sections of the hose circumference for this purpose, so that any leak which may occur initially will not leading directly to a loss of collected gas. It is thereby also conceivable that the hose may be revolvingly driven around the reversing surfaces in order to thus simplify cleaning, for example.

The gas collector may obtain the desired shape through tension cables, which partially run in the inside of the hose. In contrast, a further suitable embodiment of the present invention in which the deflection surfaces are fixed on at least one lateral, stably-shaped mounting member, is also particularly advantageous. In this way, the handling of the gas collector is simplified, in that it obtains a character independent of further components of the apparatus for three-phase separation and thus allows subsequent change of the positioning.

It is thereby also advantageous if the apparatus comprises a plurality of gas collectors adjacent one another, which are spaced an adjustable distance from one another. In this way, the gap which exists between the neighboring gas collectors may be changed without difficulty in order to avoid clogging. The distance can thereby be changed either together with the angle of inclination, whereby a large angle of inclination particularly requires a large gap, or independently from the angle of inclination.

Another advantageous variant of the present invention is provided if the outer surface is light permeable. In this way, the conversion process is promoted, in that the ambient light, particularly the sunlight, may pass essentially unhindered through the gas collector and thus also reach the bottom of the settling basin. In this way, the quality of the gas which can be produced, and therefore the cost-effectiveness of the system, may be significantly improved.

It is also particularly advantageous if the gas collector has a connection means for positioning in relation to a pressurized gas accumulator of the apparatus for three-phase separation. The gas is thereby captured in the gas collector with only a slight overpressure relative to the environment and subsequently conveyed further to the pressurized gas accumulator. For this purpose the pressurized gas accumulator may be fixed to the gas collector in a suitable position using the connection means, whereby the gas can also be conveyed from the gas collector to the pressurized gas accumulator through the connection means. In this way, the components belonging to the apparatus for three-phase separation may be made modular and connected without difficulty to one another so that an expansion of the apparatus can be readily realized.

BRIEF DESCRIPTION OF THE DRAWINGS

The invention allows various embodiments and will be described in further detail hereinafter with reference to illustrative embodiments shown in the accompanying drawing figures in which:

FIG. 1 is a perspective view of a gas collector according to the invention;

FIG. 2 is an end view of the gas collector of FIG. 1; and

DETAILED DESCRIPTION OF PREFERRED EMBODIMENTS

Figure 3:
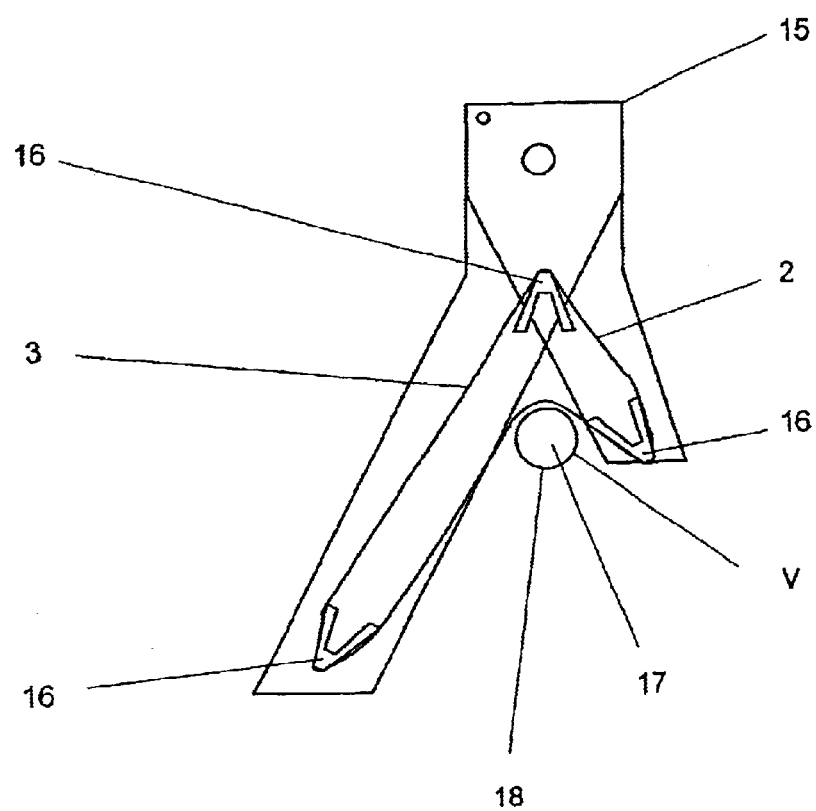
FIG. 3 is an end view of an alternate gas collector embodiment.

FIG. 1 is a perspective view of a gas collector 1 of a system according to the present invention (not shown further), for treating wastewater and sludge. The substantially angled construction of the gas collector 1 may be seen, the legs of which each form an outer surface 2, 3 on the outside and define a volume V on the inside for capturing the gas. This shape is provided simply by a tube 4, made of a film, which is stretched tight around a plurality of reversing or bending surfaces 5, 6, 7, 8 and thus acquires the desired shape. The reversing surfaces 5, 6, 7, 8 may be fixed in this case in different positions, in order to thus be able to adjust the gas collector 1 to a different shape.

This variability of shape is explained further with reference to FIG. 2, which shows the gas collector 1 in a side or end view. The deflection surfaces 5, 6, 7, 8, through which the hose 4 receives its shaping, are illustrated. Due to the simple adjustability of the deflection surfaces 5, 6, 7, 8, an angle of deflection ☐ tailored to the respective sewage sludge may particularly be set, in order to be able to reliably prevent sewage sludge introduced into the apparatus from adhering to the gas collector. If adhesion nonetheless occurs due to inattention, the angle of inclination ☐ may be changed in rapid sequence in order to thus "shake off" the adhering particles.

Simultaneously, the volume V enclosed by the gas collector 1, which is available for capturing the gas rising from below, is also determined by the altered angle of inclination ☐. The tube 4 is pretensioned in this case using a tensioning device 9 constructed as a spring element, so that the maintenance of the predetermined shape is ensured.

Furthermore, between two sections 10, 11, which form the outer surfaces 2, 3, and a further section 15, which delimits the volume V, the tube 4 is provided with a reinforcing member 12 which increases the stability of the shape.

On the outside, the gas collector 1 has a attachment member 14, equipped with a mounting plate 13, through which the deflection surfaces 5, 6, 7, 8 are fixed and the connection to a pressurized gas accumulator (not shown) of the apparatus for three-phase separation is also simultaneously provided.

FIG. 3 shows a further gas collector 15 in a side view. This differs from the gas collector 1 shown in FIG. 2 in particular due to a differing design of the reversing or bending surfaces 16, which are produced in this case by profile members and thus have increased stability and lower weight at the same time.

Furthermore, the gas collector 15 has a tensioning device 18 which is provided with a buoyant float member 17. In this way, the necessary tension of the outer surfaces 2, 3 is established automatically without an additional manual intervention being necessary for this purpose. The float 17 may thereby particularly be produced from bamboo, so that simple and cost-effective adjustment of the required buoyancy can be achieved, for example, by breaking open individual air chambers. In this way, the desired equilibrium between the weight of the gas collector 15 and the buoyant force, which counteracts this weight, may be easily achieved, the lift of the float 17 being additionally increased by the volume V of the enclosed gas.

In addition, additional counterweights may be used to achieve the equilibrium, which may in turn be at least partially filled with liquid for fine adjustment.

Figure 4:
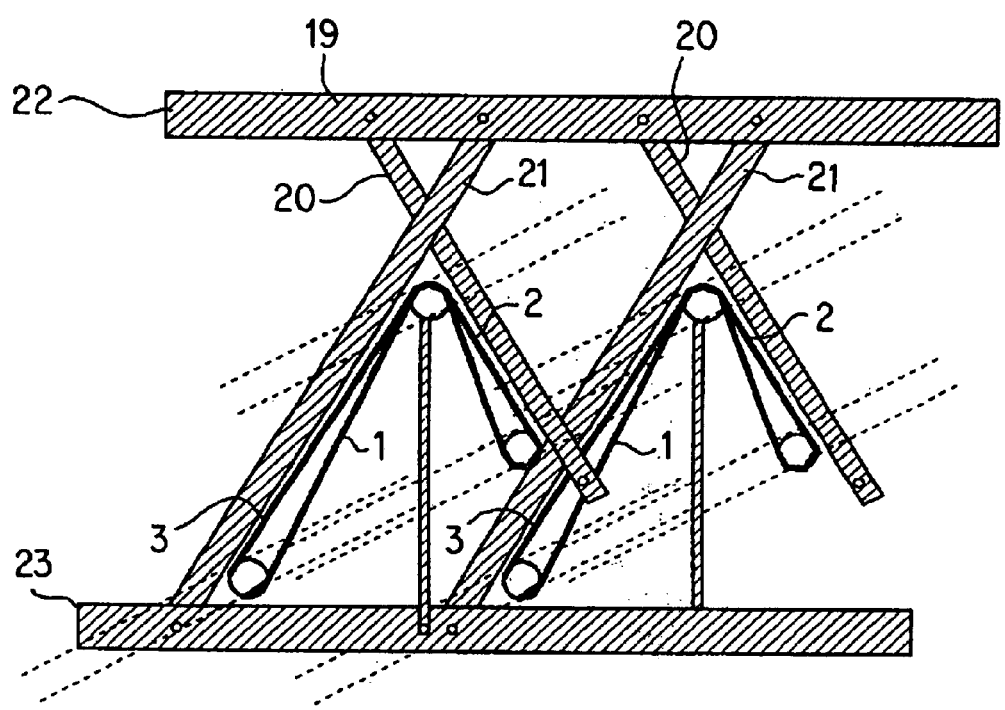
FIG. 4 is an end view of an alternate gas collector embodiment in which a distance between collectors is adjustable.

FIG. 4 illustrates an embodiment corresponding to the alternative discussed in the foregoing Summary. This embodiment is exemplary; one of ordinary skill in the art will be able to readily envision other structures which accomplish the objective of providing an ability to adjust the separation distance between gas collectors and/or their inclination angles. In this embodiment, a plurality of gas collectors 1 are held within a parallelogram lattice structure 19, with their external surfaces 2, 3 held against corresponding parallelogram elements scissoring elements 20, 21. As the parallelogram top and bottom rails 22, 23 are moved laterally with respect to one another, the separation distance between the gas collectors increases or decreases. The rate of change in the separation distance is determined by the geometry of the lattice structure.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An apparatus for three-phase separation during treatment of wastewater and sludge comprising a gas collector disposed in a settling basin for capturing gas which arises during the treatment or is introduced therein, said gas collector having an outer surface which is inclined relative to horizontal and allows the sewage sludge to slide off, wherein the outer surface has an angle of inclination which is adjustable to adapt the apparatus to treatment of different sewage sludges.

2. An apparatus according to claim 1, wherein the gas collector has two inclined outer surfaces slanted toward one another, the angles of inclination of which can be adjusted independently from one another.

3. An apparatus according to claims 1, wherein the angle of inclination of said outer surface simultaneously determines the volume of the gas collector available for receiving gas.

4. An apparatus according to claim 1, wherein a common drive is used to adjust the angle of inclination of the outer surface of each of a plurality of adjacent gas collectors.

5. An apparatus according to claim 1, wherein a drive is used to adjust the angle of inclination, and the angle of inclination is continuously variable.

6. An apparatus according to claim 1, wherein said outer surface comprises at least one flexible section.

7. An apparatus according to claim 1, wherein the outer surface comprises a gas-tight sheet material or a gas-tight fabric.

8. An apparatus according to claim 7, wherein the gas collector further comprises a tensioning device for maintaining the sheet material or fabric under tension.

9. An apparatus according to claim 8, wherein the tensioning device comprises a spring.

10. An apparatus according to claim 8, wherein the tensioning device comprises a buoyant float member.

11. An apparatus according to claim 10, wherein said float member is comprised of bamboo.

12. An apparatus according to claim 1, wherein the gas collector comprises a movable surface supported on a plurality of reversing surfaces; said movable surface comprising a first section, which forms said outer surface, and a second, set-back section for receiving gas to be collected.

13. An apparatus according to claim 6, wherein said outer surface is formed by a tube.

14. An apparatus according to claim 12, wherein said reversing surfaces are affixed to at least one lateral, stably-formed mounting member.

15. An apparatus according to claim 1, wherein said apparatus comprises a plurality of neighboring gas collectors spaced apart from one another, and a distance between neighboring gas collectors is adjustable.

16. An apparatus according to claim 1, wherein said outer surface is light permeable.

17. An apparatus according to claim 1, further comprising a connection means for connecting the gas collector to a pressurized gas accumulator.

* * * * *